(12) United States Patent
Bui et al.

(10) Patent No.: US 9,713,588 B2
(45) Date of Patent: *Jul. 25, 2017

(54) NITROCELLULOSE-FREE NAIL POLISH COMPOSITIONS

(75) Inventors: Hy Si Bui, Piscataway, NJ (US);
Chunhua Li, Hillsborough, NJ (US);
Sarah Fairneny, Garwood, NJ (US);
Luis Ortega, East Brunswick, NJ (US);
Mohamed Kanji, Edison, NJ (US);
Ram Hariharan, Springfield, NJ (US)

(73) Assignee: L'OREAL, Paris (FR)

(*) Notice: Subject to any disclaimer, the term of this patent is extended or adjusted under 35 U.S.C. 154(b) by 202 days.

This patent is subject to a terminal disclaimer.

(21) Appl. No.: 13/882,663

(22) PCT Filed: Oct. 31, 2011

(86) PCT No.: PCT/US2011/058515
§ 371 (c)(1),
(2), (4) Date: Apr. 30, 2013

(87) PCT Pub. No.: WO2012/061265
PCT Pub. Date: May 10, 2012

(65) Prior Publication Data
US 2013/0224134 A1    Aug. 29, 2013

Related U.S. Application Data

(60) Provisional application No. 61/409,387, filed on Nov. 2, 2010.

(51) Int. Cl.
| *A61Q 3/02* | (2006.01) |
| *A61K 8/02* | (2006.01) |
| *A61K 8/31* | (2006.01) |
| *A61K 8/37* | (2006.01) |
| *A61K 8/92* | (2006.01) |
| *A61K 33/06* | (2006.01) |
| *A61K 8/90* | (2006.01) |
| *A61K 8/86* | (2006.01) |
| *A61K 8/84* | (2006.01) |
| *A61K 8/87* | (2006.01) |
| *A61K 8/58* | (2006.01) |
| *A61K 8/40* | (2006.01) |
| *A61K 8/81* | (2006.01) |
| *A61K 8/88* | (2006.01) |

(52) U.S. Cl.
CPC ................ *A61K 8/90* (2013.01); *A61K 8/40* (2013.01); *A61K 8/585* (2013.01); *A61K 8/8164* (2013.01); *A61K 8/84* (2013.01); *A61K 8/86* (2013.01); *A61K 8/87* (2013.01); *A61K 8/88* (2013.01); *A61Q 3/02* (2013.01); *A61K 2800/594* (2013.01)

(58) Field of Classification Search
CPC ... A61K 8/90; A61K 8/86; A61K 8/84; A61K 8/585; A61K 8/8164; A61K 8/88; A61K 8/87; A61K 2800/594; A61K 31/15; A61Q 3/02

USPC ........................................................ 424/61
See application file for complete search history.

(56) References Cited

U.S. PATENT DOCUMENTS

| 3,639,122 | A | * | 2/1972 | Shimizu | G03G 5/142 101/460 |
| 3,677,694 | A | * | 7/1972 | Sugimoto et al. | D06M 13/127 8/127.6 |
| 3,679,348 | A | * | 7/1972 | Asahi et al. | D06M 13/127 8/115.7 |
| 4,409,203 | A | * | 10/1983 | Gordon | A61K 8/731 424/61 |
| 4,749,564 | A | * | 6/1988 | Faryniarz et al. | 424/61 |
| 4,897,261 | A | | 1/1990 | Yamazaki et al. | |
| 5,217,813 | A | | 6/1993 | Roser et al. | |
| 5,391,636 | A | | 2/1995 | Schilling | |
| 5,747,018 | A | * | 5/1998 | Valenty | A61K 8/8164 424/61 |
| 6,254,878 | B1 | * | 7/2001 | Bednarek et al. | 424/401 |
| 6,534,181 | B2 | * | 3/2003 | Luttrull | H05K 1/0326 428/413 |

(Continued)

FOREIGN PATENT DOCUMENTS

| EP | 0 424 112 A2 | 4/1991 |
| FR | 2 789 896 A1 | 8/2000 |

(Continued)

OTHER PUBLICATIONS

Spychaj et al. (Water-thinned epoxy coating compositions, Polimery fluoropolymer (1993), 38(4-5), 200-4).*
Oishi, JP 04120148 A; pub. 1992; manual translation by Wessen Debela, PTO-15-2370 (Mar. 2015), 59 pages.*
Spychaj et al., Water-Thinnable Epoxy Coating Compositions, translation by FLS, Inc. (Nov. 2015), 19 pages.*
Spychaj et al., Wodorozcienczalne powlokowe kompozycje epoksydowe (Water-Thinnable epoxy coating compositions), Polimery—Tworzyw A Wielkoczt\Steczowe (1993), pp. 200-204.*
U.S. Appl. No. 13/882,644, filed Apr. 30, 2013, Bui, et al.
International Preliminary Report on Patentability Issued May 16, 2013 in PCT/US2011/058515.

(Continued)

Primary Examiner — Ernst V Arnold
Assistant Examiner — Miriam A Levin
(74) Attorney, Agent, or Firm — Oblon, McClelland, Maier & Neustadt, L.L.P.

(57) ABSTRACT

The present invention relates to a nail polish composition comprising: at least one high gloss film forming agent chosen from a styrene maleic anhydride copolymer; at least one co-film forming agent chosen from an epoxy resin; at least one reactive agent chosen from a combination of a polyalkyleneamine and a polyurethane, at least one polyalkyleneamine, and at least one alkoxysilane comprising at least one solubilizing functional group; at least one solvent chosen from at least one volatile solvent and water; optionally, at least one plasticizer; and optionally, at least one colorant, wherein the composition does not require use of nitrocellulose and can be used to makeup or protect nails.

24 Claims, No Drawings

(56) References Cited

U.S. PATENT DOCUMENTS

| | | | |
|---|---|---|---|
| 6,582,684 B1 * | 6/2003 | Abrahamson | 424/63 |
| 6,953,584 B1 | 10/2005 | Samain et al. | |
| 7,740,664 B2 | 6/2010 | Benabdillah | |
| 8,475,816 B2 | 7/2013 | Bui et al. | |
| 2006/0216250 A1 | 9/2006 | Schultz et al. | |
| 2007/0093393 A1 | 4/2007 | Navarrete et al. | |
| 2007/0189995 A1 | 8/2007 | Weber et al. | |
| 2007/0189996 A1 | 8/2007 | Weber et al. | |
| 2008/0206173 A1 | 8/2008 | Weber et al. | |
| 2008/0226576 A1 | 9/2008 | Benabdillah et al. | |
| 2009/0081261 A1 | 3/2009 | Thevenet | |
| 2009/0214455 A1 | 8/2009 | Blin et al. | |
| 2009/0263338 A1 | 10/2009 | Rolland et al. | |
| 2010/0278766 A1 * | 11/2010 | Ortega et al. | 424/61 |
| 2010/0330017 A1 | 12/2010 | Bui et al. | |
| 2010/0330024 A1 | 12/2010 | Bui et al. | |
| 2011/0020260 A1 | 1/2011 | Bui et al. | |
| 2011/0021681 A1 | 1/2011 | Bui et al. | |
| 2011/0083284 A1 * | 4/2011 | Suddaby | A61K 8/19 8/405 |
| 2011/0150802 A1 | 6/2011 | Bui et al. | |
| 2011/0150805 A1 | 6/2011 | Kergosien et al. | |
| 2011/0150806 A1 | 6/2011 | Bui et al. | |
| 2011/0150807 A1 | 6/2011 | Bui et al. | |
| 2011/0223122 A1 | 9/2011 | Bui et al. | |
| 2011/0305655 A1 | 12/2011 | Bui et al. | |
| 2013/0034513 A1 | 2/2013 | Samain | |
| 2013/0039874 A1 | 2/2013 | Li et al. | |

FOREIGN PATENT DOCUMENTS

| | | |
|---|---|---|
| FR | 2 910 305 A1 | 6/2008 |
| FR | 2 954 151 A1 | 6/2011 |
| FR | 2 954 155 A1 | 6/2011 |
| FR | 2 954 156 A1 | 6/2011 |
| JP | 04120148 A * | 4/1992 |
| JP | 08028743 A * | 2/1996 |
| JP | 09202715 A * | 8/1997 |
| JP | 4221273 B2 * | 2/2009 |
| WO | WO 2008/046763 A1 | 4/2008 |

OTHER PUBLICATIONS

Written Opinion of the International Searching Authority Issued Jul. 2, 2012 in PCT/US2011/058515, 4 pages.

International Search Report Issued Jul. 2, 2012 in PCT/US11/58515 Filed Oct. 31, 2011, 2 pages.

\* cited by examiner

NITROCELLULOSE-FREE NAIL POLISH COMPOSITIONS

CROSS-REFERENCE TO RELATED APPLICATION

This application claims the benefit of the filing date of U.S. Provisional Application No. 61/409,387 filed Nov. 2, 2010, the contents of which are incorporated by reference.

FIELD OF THE INVENTION

The present invention relates to nail polish compositions which do not require the use of nitrocellulose. Such nail polish compositions are safer to manufacture, and have comparable or better adhesion properties than, traditional nail polish compositions.

DISCUSSION OF THE BACKGROUND

Nail polish compositions traditionally contain a large amount of nitrocellulose, primarily because nitrocellulose provides good adhesion of the compositions to nails upon application. That is, nitrocellulose is the preferred adhesive agent for use in nail polish compositions, and constitutes the "gold standard" of adhesive agents in nail polish compositions. However, nitrocellulose has drawbacks, particularly with respect to consumer safety. Also, nail polish compositions containing nitrocellulose can have poor long wear characteristics. Further, nitrocellulose does not impart high gloss. As a result, alternatives to nitrocellulose-based nail polish compositions have been sought. Unfortunately, to date, such alternatives have been elusive, and commercial nail polish compositions typically contain large amounts of nitrocellulose.

There remains a need for nail polish compositions which are safe, glossy, and adhere well to nails and, ideally, contain minimal, if any, amounts of nitrocellulose.

SUMMARY OF THE INVENTION

The present invention relates to a nail polish composition, comprising:
a. at least one high gloss film forming agent chosen from a styrene maleic anhydride copolymer;
b. at least one co-film forming agent chosen from an epoxy resin;
c. at least one reactive agent chosen from:
   i. a combination of a polyalkyleneamine and a polyurethane;
   ii. at least one polyalkyleneamine; and
   iii. at least one alkoxysilane comprising at least one solubilizing functional group;
d. at least one solvent chosen from at least one volatile solvent and water;
e. optionally, at least one plasticizer; and
f. optionally, at least one colorant,
wherein the composition does not require use of nitrocellulose.

The present invention further relates to a method of making up finger nails comprising applying the above-described composition onto the nails.

It has been surprisingly found by the inventors that the above-described composition, when applied onto finger nails, yields a nail polish coating having exceptional adhesion, long wear and high gloss, in the absence of nitrocellulose.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Volatile", as used herein, means having a flash point of less than about 100° C.

"Transfer resistance" as used herein refers to the quality exhibited by compositions that are not readily removed by contact with another material, such as, for example, an item of clothing. Transfer resistance may be evaluated by any method known in the art for evaluating such. For example, transfer resistance of a composition may be evaluated by a modified "kiss" test. The modified "kiss" test may involve application of the composition to a fingernail followed by rubbing a material, for example, a sheet of paper, against the nail after expiration of a certain amount of time following application, such as 5 minutes after application. Similarly, transfer resistance of a composition may be evaluated by the amount of product transferred from a wearer to any other substrate, such as transfer from the nail of an individual to a sleeve when putting on clothing after the expiration of a certain amount of time following application of the composition to the nail. The amount of composition transferred to the substrate (e.g., sleeve or paper) may then be evaluated and compared. For example, a composition may be transfer resistant if a majority of the product is left on the wearer's nails. Further, the amount transferred may be compared with that transferred by other compositions, such as commercially available compositions. In a preferred embodiment of the present invention, little or no composition is transferred to the substrate from the nail.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to nails and evaluating the color of the composition after an extended period of time. For example, the color of a composition may be evaluated immediately following application to nails and these characteristics may then be re-evaluated and compared after a certain amount of time. Further, these characteristics may be evaluated with respect to other compositions, such as commercially available compositions.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The compositions and methods of the present invention can comprise, consist of, or consist essentially of the essential elements and limitations of the invention described herein, as well as any additional or optional ingredients, components, or limitations described herein or otherwise useful.

High Gloss Film Forming Agents

According to the present invention, the nail polish composition comprises at least one high gloss film forming agent chosen from a styrene maleic anhydride copolymer. "Styrene maleic anhydride copolymer," as used herein, means any polymer obtained by copolymerization of one or more maleic anhydride comonomers and of one or more styrene comonomers, the maleic anhydride comonomers optionally being partially hydrolysed or completely hydrolysed.

In general, it is known that while styrene maleic anhydride copolymers have high gloss, they have a tendency to be too brittle. Their use, therefore, has typically been limited to those applications where brittleness is not a concern. The inventors, however, have surprisingly found that styrene maleic anhydride copolymers, when mixed with certain softer co-film forming agents, may then be effectively employed in nail polish compositions in spite of their conventional brittle tendencies. It has been found that such combinations allow for a nail composition to be formulated, in the absence of nitrocellulose, having long wear, good adhesion and high gloss properties, above and beyond conventional nail polish compositions containing nitrocellulose.

According to preferred embodiments, the styrene maleic anhydride copolymer has a molar fraction of maleic anhydride units of between 0.1 and 0.95, more preferably between 0.4 and 0.9.

According to preferred embodiments, the styrene maleic anhydride copolymer has styrene and maleic anhydride monomers in a molar ratio of 1:3 to 3:1, more preferably in a molar ratio of 1:2 to 2:1, and more preferably in a molar ratio of about 1:1, including all ranges and subranges therebetween such as 1.2:1 and 1.4:1.

According to preferred embodiments, the styrene maleic anhydride copolymer has a weight-average molecular weight ranging from about 1,000 to 200,000, preferably from about 5,000 to 100,000, and most preferably from about 10,000 to 50,000.

According to preferred embodiments, the styrene maleic anhydride copolymer has a glass transition temperature (Tg) ranging from about 100° C. to 175° C., preferably from about 125° C. to 160° C., and more preferably from about 135° C. to 155° C.

Preferred styrene maleic anhydride copolymers for use in the base coat composition of the present invention include non-esterified styrene maleic anhydride copolymers. Suitable examples of non-esterified styrene maleic anhydride copolymers include, but are not limited to, Hercules products Scripset® 520 (styrene/maleic anhydride copolymer), as well as liquid solutions containing this polymer such as, for example, imPress® SC-700 (sodium solution) and imPress® SC-720 (ammonium solution); Atofina products such as the styrene/maleic anhydride (50/50) copolymer, in the form of an ammonium salt at 30% in water, sold under the reference SMA1000H® or the styrene/maleic anhydride (50/50) copolymer, in the form of a sodium salt at 40% in water, sold under the reference SMA1000HNa®; and Sartomer products such as SMA®1000 (styrene/maleic anhydride (50/50) copolymer having a Tg of 155° C., a Mn of 2000, and a Mw of 5500), SMA®2000 (styrene/maleic anhydride (2:1) copolymer having a Tg of 135° C., a Mn of 3000, and a Mw of 7500), and SMA®2021 (styrene/maleic anhydride (2:1) copolymer having a Tg of 155° C., a Mn of 12,000, and a Mw of 21,000).

The styrene maleic anhydride copolymers of the present invention may also be esterified. "Esterified styrene maleic anhydride copolymer" as used herein means a styrene maleic anhydride copolymer which has been esterified using a small alcohol compound. Preferably, the small alcohol compound has fewer than 8 carbon atoms, preferably fewer than five carbon atoms, and more preferably fewer than four carbon atoms. For example, a styrene maleic anhydride copolymer can be esterified via standard esterification techniques using butanol, isobutanol, propanol, isopropanol, ethanol, methanol or any mixture of these alcohols, to produce an esterified styrene maleic anhydride copolymer. It should be noted, however, that in the event an esterified styrene maleic anhydride copolymer is employed, it cannot be completely esterified. Preferred styrene maleic anhydride copolymers are those which are non-esterified.

In accordance with preferred embodiments, the at least one high gloss film-forming agent of the present invention is preferably present in the composition in an amount of from about 1% to about 40% by weight, preferably from about 5% to about 30% by weight, and more preferably from about 10% to about 20% of the total weight of the composition, including all ranges and subranges therebetween, all weights based on the total weight of the nail polish composition.

Co-Film Forming Agents

The nail polish composition of the present invention further comprises at least one co-film forming agent chosen from an epoxy resin. Particularly preferred epoxy resins include, but are not limited to, tosylamide epoxy resins such as those sold under the Polytex name by Estron Chemical, Inc. (for example, E-75, E-100 and NX-55). Epoxy resins have been shown to provide good adhesion and are less brittle than the high gloss film forming agents disclosed above.

Other co-film forming agents that may be employed in combination with an epoxy resin include, for example, radical polymers, polycondensates and polymers of natural origin.

Examples of suitable co-film forming agents include, but are not limited to, vinyl polymers such as, for example, polyvinyl butyral, acrylic (co)polymers, acrylic resins, styrene resins, acrylate-styrene resins, vinyl resins, vinyl copolymers, polyurethanes, polyesters, alkyd resins, cellulose polymers, such as nitrocellulose, cellulose esters, such as cellulose acetate, cellulose acetate propionate or cellulose acetate butyrate, resins resulting from the condensation of formaldehyde with an arylsulphonamide, and their mixtures. Other suitable co-film forming polymers may also include film formers which are more compatible with water. Examples of such film formers include, but are not limited to, starches and derivatives thereof, natural or synthetic gums and derivatives thereof, water soluble adhesives. Particularly preferred co-film forming agents are resin film forming agents, particularly polyester, acrylic and acrylic resins.

Specific examples of useful (meth)acrylic polymers or resins include, but are not limited to, copolymers of methyl methacrylate with butyl acrylate, butyl methacrylate, isobutyl methacrylate, or isobornyl methacrylate (e.g., PARALOID DM-55, PARALOID B48N, PARALOID B66, ELVACITE 2550), copolymers of isobutylmethacrylate and butyl methacrylate (e.g., ELVACITE 2046), and isobutyl methacrylate polymers (e.g., PARALOID B67).

Specific examples of polyester resins include, but are not limited to, polyester resins formed by reacting a polyhydric alcohol with a polybasic acid, e.g., phthalic acid such as, for example, UNIPLEX 670-P polyester resin, which is available from Unitex Chemical Corporation and which is a polyester resin obtained by reacting trimellitic acid, neopentyl glycol, and adipic acid.

As stated above, optionally-esterified styrene maleic anhydride copolymers are known to be brittle. However, it has been surprisingly found that combining them with at least one co-film forming agent chosen from an epoxy resin effectively renders the optionally-esterified styrene maleic anhydride copolymer less brittle, thereby allowing it to be incorporated into nail polish compositions having long wear, good adhesion and high gloss properties, without requiring the use of nitrocellulose. Accordingly, it is preferred that the at least one co-film forming agent chosen from an epoxy resin has a glass transition temperature (Tg) of less than about 100° C., preferably less than about 80° C.

According to preferred embodiments, the at least one co-film forming agent chosen from an epoxy resin is present in the compositions of the present invention in an amount ranging from about 0.1 to about 50% by weight, more preferably from about 1 to about 40% by weight, and most preferably from about 10 to about 30% by weight, including all ranges and subranges therebetween, all weights based on the total weight of the nail polish composition.

According to preferred embodiments, the compositions of the present invention contain weight ratios of styrene maleic anhydride copolymer to at least one co-film forming agent chosen from an epoxy resin ranging from about 1 to 1, preferably from about 2 to 1, and more preferably from about 3 to about 1, including all ranges and subranges therebetween.

According to yet other preferred embodiments, the compositions of the present invention contain weight ratios of styrene maleic anhydride copolymer to at least one co-film forming agent chosen from an epoxy resin in a range of about 1 to 1, preferably about 1 to 2, and more preferably about 1 to 3, including all ranges and subranges therebetween.

Reactive Agents

The nail polish composition of the present invention comprises at least one reactive agent chosen from at least one polyaklyleneimine, a combination of a polyalkyleneimine and a polyurethane, and at least one alkoxysilane comprising at least one solubilizing functional group.

Polyalkyleneimine

The nail polish composition of the present invention contains at least one reactive agent which may be chosen from at least one polyalkyleneamine. Non-limiting examples of polyalkyleneamines include polyethyleneimines such as Lupasol® products commercially available from BASF. Suitable examples of Lupasol® polyethyleneimines include Lupasol® PS, Lupasol® PL, Lupasol® PR8515, Lupasol® G20, Lupasol® G35 as well as Lupasol® SC Polyethyleneimine Reaction Products (such as Lupasol® SC-61B, Lupasol® SC-62J, and Lupasol® SC-86X). Other non-limiting examples of polyethyleneimines which may be used in the composition according to the present invention are the Epomin® products commercially available from Aceto. Suitable examples of Epomin® polyethyleneimines include Epomin® SP-006, Epomin® SP-012, Epomin® SP-018, and Epomin® P-1000. These examples include substituted polyethyleneimines.

Polyalkyleneimine and Polyurethane

The at least one reactive agent of the present invention may also comprise at least one reactive agent chosen from a combination of a polyalkyleneimine and a polyurethane. The at least one polyalkylemeimine may be chosen from the compounds described above.

With respect to the polyurethane, the polyurethane may be commercially available as an aqueous dispersion. "Aqueous polyurethane dispersion" as used herein means the aqueous polyurethane dispersions disclosed in U.S. Pat. No. 7,445,770 and/or U.S. Pat. No. 7,452,770, the entire contents of both of which are hereby incorporated by reference.

More specifically, aqueous polyurethane dispersions are preferably the reaction products of:

A) a prepolymer according to the formula:

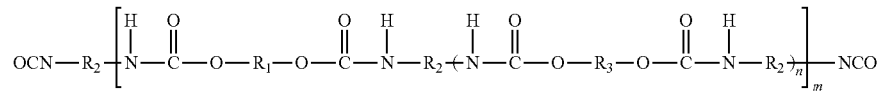

wherein $R_1$ represents a bivalent radical of a dihydroxyl functional compound, $R_2$ represents a hydrocarbon radical of an aliphatic or cycloaliphatic polyisocyanate, $R_3$ represents a radical of a low molecular weight diol, optionally substituted with ionic groups, n is from 0 to 5, and m is >1;

B) at least one chain extender according to the formula: $H_2N-R_4-NH_2$ wherein $R_4$ represents an alkylene or alkylene oxide radical not substituted with ionic or potentially ionic groups; and C) at least one chain extender according to the formula: $H_2N-R_5-NH_2$ wherein $R_5$ represents an alkylene radical substituted with ionic or potentially ionic groups.

Suitable dihydroxyl compounds for providing the bivalent radical $R_1$ include those having two hydroxy groups and having number average molecular weights of from about 700 to about 16,000, and preferably from about 750 to about 5000. Examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. The polyester polyols, polyether polyols and polyhydroxy polycarbonates are preferred. Mixtures of various such compounds are also within the scope of the present invention.

Suitable polyisocyanates for providing the hydrocarbon radical $R_2$ include organic diisocyanates having a molecular weight of from about 112 to 1,000, and preferably from about 140 to 400. Preferred diisocyanates are those represented by the general formula $R_2(NCO)_2$ indicated above in which $R_2$ represents a divalent aliphatic hydrocarbon group having from 4 to 18 carbon atoms, a divalent cycloaliphatic hydrocarbon group having from 5 to 15 carbon atoms, a divalent araliphatic hydrocarbon group having from 7 to 15 carbon atoms or a divalent aromatic hydrocarbon group having 6-15 carbon atoms. Examples of the organic diisocyanates which are suitable include tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or (TDI), bis-(4-isocyanatocyclohexyl)-methane, 1,3- and 1,4-bis(isocyanatomethyl)-cyclohexane, bis-(4-isocyanato-3-methyl-cyclohexyl)-methane, isomers of toluene diisocyanate (TDI) such as 2,4-diisocyanatotoluene, 2,6-diisocyanatotoluene, mixtures of these isomers, hydrogenated TDI, 4,4'-diisocyanato diphenyl methane and its isomeric mixtures with 2,4'- and optionally 2,2'-diisocyanato diphenylmethane, and 1,5-diisocyanato naphthalene. Mixtures of diisocyanates can, of course, be used. Preferred diisocyanates are aliphatic and cycloaliphatic diisocyanates. Particularly preferred are 1,6-hexamethylene diisocyanate and isophorone diisocyanate.

"Low molecular weight diols" in the context of $R_3$ means diols having a molecular weight from about 62 to 700, preferably 62 to 200. They may contain aliphatic, alicyclic or aromatic groups. Preferred compounds contain only aliphatic groups. The low molecular weight diols having up to about 20 carbon atoms per molecule include ethylene glycol, diethylene glycol, propane 1,2-diol, propane 1,3-diol, butane 1,4-diol, butylene 1,3-glycol, neopentyl glycol, butyl ethyl propane diol, cyclohexane diol, 1,4-cyclohexane dimethanol, hexane 1,6-diol, bisphenol A (2,2-bis(4-hydroxyphenyl) propane), hydrogenated bisphenol A (2,2-bis(4-hydroxycyclohexyl)propane), and mixtures thereof. Optionally, the low molecular weight diols may contain ionic or potentially ionic groups. Suitable lower molecular weight diols containing ionic or potentially ionic groups are those disclosed in U.S. Pat. No. 3,412,054, the contents of which is hereby incorporated by reference. Preferred compounds include dimethylol butanoic acid (DMBA), dimethylol propionic acid (DMBA) and carboxyl-containing caprolactone polyester diol. If lower molecular weight diols containing ionic or potentially ionic groups are used, they are preferably used in an amount such that <0.30 meq of COOH per gram of polyurethane in the polyurethane dispersion are present.

The prepolymer is chain extended using two classes of chain extenders. First, compounds having the formula: $H_2N$—$R_4$—$NH_2$ wherein $R_4$ represents an alkylene or alkylene oxide radical not substituted with ionic or potentially ionic groups. Alkylene diamines include hydrazine, ethylenediamine, propylenediamine, 1,4-butylenediamine and piperazine. The alkylene oxide diamines include 3-{2-[2-(3-aminopropoxy)ethoxy]ethoxy}propylamine (also known as dipropylamine diethyleneglycol or DPA-DEG available from Tomah Products, Milton, Wis.), 2-methyl-1,5-pentanediamine (Dytec A from DuPont), hexane diamine, isophorone diamine, and 4,4-methylenedi-(cyclohexylamine), and the DPA-series ether amines available from Tomah Products, Milton, Wis., including dipropylamine propyleneglycol, dipropylamine dipropyleneglycol, dipropylamine tripropyleneglycol, dipropylamine poly(propylene glycol), dipropylamine ethyleneglycol, dipropylamine poly(ethylene glycol), dipropylamine 1,3-propane diol, dipropylamine 2-methyl-1,3-propane diol, dipropylamine 1,4-butane diol, dipropylamine 1,3-butane diol, dipropylamine 1,6-hexane diol and dipropylamine cyclohexane-1,4-dimethanol. Mixtures of the listed diamines may also be used.

The second class of chain extenders are compounds having the formula: $H_2N$—$R_5$—$NH_2$ wherein $R_5$ represents an alkylene radical substituted with ionic or potentially ionic groups. Such compounds have an ionic or potentially ionic group and two groups that are reactive with isocyanate groups. Such compounds contain two isocyanate-reactive groups and an ionic group or group capable of forming an ionic group. The ionic group or potentially ionic group can be selected from the group consisting of ternary or quaternary ammonium groups, groups convertible into such a group, a carboxyl group, a carboxylate group, a sulfonic acid group and a sulfonate group. The at least partial conversion of the groups convertible into salt groups of the type mentioned may take place before or during the mixing with water. Specific compounds include diaminosulfonates, such as for example the sodium salt of N-(2-aminoethyl)-2-aminoethane sulfonic acid (AAS) or the sodium salt of N-(2-aminoethyl)-2-aminopropionic acid.

The polyurethane according to the present invention may also include compounds which are situated in each case at the chain ends and terminate said chains (chain terminators) as described in U.S. Pat. No. 7,445,770 and/or U.S. Pat. No. 7,452,770.

Preferably, the polyurethane may also be employed in the compositions of the present invention in the form of an aqueous dispersion, wherein the aqueous polyurethane dispersion has a viscosity of less than 2000 mPa·s at 23 C, preferably less than 1500, preferably less than 1000, including all ranges and subranges therebetween. Further preferably, the aqueous polyurethane dispersion has a glass transition temperature below 0° C.

Also preferably, the aqueous polyurethane dispersion has a solids content based on the weight of the dispersion of from 20% to 60%, preferably from 25% to 55% and preferably from 30% to 50%, including all ranges and subranges therebetween.

Suitable polyurethane compounds for use in the present invention include those available as, but not limited to, aqueous polyurethane dispersions sold under the BAYCUSAN® name by Bayer such as, for example, BAYCUSAN® C1000 (polyurethane-34), BAYCUSAN® C1001 (polyurethane-34), BAYCUSAN® C1003 (polyurethane-32), and BAYCUSAN® C1004 (polyurethane-35).

Alkoxysilanes Comprising at Least One Solubilizing Functional Group

The nail polish compositions of the present invention may also contain at least one reactive agent chosen from at least one alkoxysilanes comprising at least one solubilizing functional group. As used herein, the term "at least one solubilizing functional group" means any functional chemical group facilitating the bringing into solution of the alkoxysilane in the solvent or in a combination of solvents of the composition, for example, in solvents chosen from water and water-alcoholic mixtures.

Suitable solubilizing functional groups for use in accordance with the present disclosure include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyle, and polyether groups.

The at least one alkoxysilane present in the composition comprises at least one solubilizing functional group, which may be identical or different, such as those previously defined.

The at least one alkoxysilane comprising at least one solubilizing functional group present in the composition of the present disclosure may comprise at least one silicon atom, for example, one silicon atom.

The at least one alkoxysilane comprising at least one solubilizing functional group present in the composition may, in at least one embodiment, comprise two or three alkoxy functions. In another embodiment, the alkoxy functional groups are chosen from methoxy and ethoxy functional groups.

According to a further embodiment, the at least one alkoxysilane comprising at least one solubilizing functional group present in the composition of the present disclosure is chosen from compounds of formula (I):

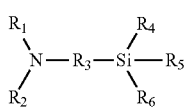

(I)

wherein:

$R_4$ is chosen from halogen atoms, OR' groups, and $R_{11}$ groups;

$R_5$ is chosen from halogen atoms, OR" groups, and $R_{12}$ groups;

$R_6$ is chosen from halogen atoms, OR'" groups, and $R_{13}$ groups;

$R_1$, $R_2$, $R_3$, R', R", R'", $R_{11}$, $R_{12}$, and $R_{13}$, which may be identical or different, are chosen from linear and branched, saturated and unsaturated hydrocarbon groups, optionally bearing at least one additional chemical group, wherein $R_1$, $R_2$, R', R", and R'" may also be chosen from hydrogen; at least two groups $R_4$, $R_5$, and $R_6$ are different from $R_{11}$, $R_{12}$, and $R_{13}$, and at least two groups R', R", and R'" are not hydrogen.

In at least one embodiment, the $R_1$, $R_2$, R', $R'_1$, $R'_2$, $R'_3$, R", and R'" groups are chosen from $C_1$-$C_{12}$ alkyl, $C_6$-$C_{14}$ aryl, $C_1$-$C_8$ alkyl-$C_6$-$C_{14}$ aryl, and $C_6$-$C_{14}$ aryl-$C_1$-$C_8$-alkyl radicals.

According to a second embodiment of the present disclosure, the at least one alkoxysilane comprising at least one solubilizing functional group present in the composition is chosen from compounds of formula (II):

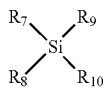

(II)

wherein:

$R_9$ is chosen from halogen atoms and $OR'_9$ groups and $R_{10}$ is chosen from halogen atoms and $OR'_{10}$ groups; wherein at least one of $R_9$ and $R_{10}$ is not a halogen;

$R'_9$ and $R'_{10}$, which may be identical or different, are chosen from hydrogen, and linear and branched, saturated and unsaturated $C_1$-$C_{14}$ hydrocarbon groups; wherein at least one of $R_9$ and $R_{10}$ is not hydrogen;

$R_7$ is a non hydrolyzable functional group providing a cosmetic effect, and $R_8$ is a non hydrolyzable functional group bearing at least one function chosen from: amines, carboxylic acids and salts thereof, sulfonic acids and salts thereof, polyols such as glycol, polyethers such as polyalkylene ether, and phosphoric acids and salts thereof.

As used herein, the term "functional group providing a cosmetic effect" means a group derived from an entity chosen from reducing agents, oxidizing agents, coloring agents, polymers, surfactants, antibacterial agents, and UV absorbing filters.

In at least one embodiment, the functional group providing a cosmetic effect is a group derived from a coloring agent.

According to a third embodiment of the present disclosure, the at least one alkoxysilane comprising at least one solubilizing functional group present in the composition of the present disclosure is chosen from compounds of formula (III):

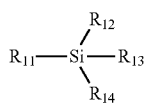

(III)

wherein:

$R_{12}$ is chosen from halogen atoms, $OR'_{12}$ groups, and $R_o$ groups;

$R_{13}$ is chosen from halogen atoms, $OR'_{13}$ groups, and $R'_o$ groups;

$R_{14}$ is chosen from halogen atoms, $OR'_{14}$ groups, and $R''_o$ groups;

wherein at least two groups $R_{12}$, $R_{13}$, and $R_{14}$ are different from $R_o$, $R'_o$, and $R''_o$ groups;

$R_{11}$ is a group chosen from groups bearing at least one function chosen from: carboxylic acids and salts thereof, sulfonic acids and salts thereof, and polyalkylethers; and Ro, R'o, R"o, $R'_{12}$, $R'_{13}$, and $R'_{14}$, which may be identical or different, are chosen from linear and branched, saturated and unsaturated, $C_1$-$C_{14}$ hydrocarbon groups optionally bearing at least one additional chemical functional group chosen from: carboxylic acids and salts thereof, sulfonic acids and salts thereof, and polyalkylether functions, wherein $R'_{12}$, $R'_{13}$, and $R_{14}$ may also be chosen from hydrogen, and wherein at least two of the groups $R'_{12}$, $R'_{13}$, and $R'_{14}$ are not hydrogen.

In at least one embodiment, the $R'_{12}$, $R'_{13}$, $R'_{14}$, $R_o$, $R'_o$, $R''_o$ groups are chosen from $C_1$-$C_{12}$ alkyl groups, $C_6$-$C_{14}$ aryl groups, $C_1$-$C_8$ alkyl-$C_6$-$C_{14}$ aryl groups, and $C_6$-$C_{14}$ aryl-$C_1$-$C_8$ alkyl groups.

According to another embodiment of the present disclosure, the at least one alkoxysilane comprising at least one solubilizing functional group present in the composition of the present disclosure is chosen from compounds of formula (IV):

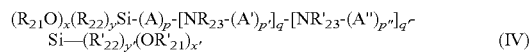

(IV)

wherein:

$R_{21}$, $R_{22}$, $R'_{21}$, and $R'_{22}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups, x is an integer ranging from 1 to 3, y=3-x, x' is an integer ranging from 1 to 3, y'=3-x', p=0 or 1, p'=0 or 1, p"=0 or 1, q=0 or 1,
q'=0 or 1,
wherein at least one of q or q' is not equal to zero,
A, A', and A", which may be identical or different, are chosen from linear and branched C1-C20 alkylene divalent radicals, and
R23 and R'23, which may be identical or different, are chosen from hydrogen and linear and branched, saturated and unsaturated hydrocarbon chains, optionally comprising at least one heteroatom, optionally interrupted by or substituted with at least one entity chosen from: ether, C1-C20 alcohol ester, amine, carboxyl, alkoxysilane, C6-C30 aryl, hydroxyl, and carbonyl groups, and aromatic, heterocyclic, and non-heterocyclic rings, optionally substituted with at least one group chosen from C3-C20 alcohol ester, amine, amide, carboxyl, alkoxysilane, hydroxyl, carbonyl, and acyl groups.

As defined above, R21, R22, R'21, and R'22, which may be identical or different, may be chosen from hydrocarbon chains. As used herein, the term "hydrocarbon chain" means, for example, a chain comprising from 1 to 10 carbon atoms.

Likewise, R23 and R'23 may be chosen from hydrocarbon chains. In such an embodiment, the hydrocarbon chains may comprise from 1 to 10 carbon atoms.

According to one embodiment, the aromatic ring comprises from 6 to 30 carbon atoms. In another embodiment, the aromatic ring is an optionally substituted phenyl radical.

In at least one embodiment, in formula (IV) above:
R21=R'21,
R22=R'22,
x=x',
y=y',
p=p',
A=A',
q=1, and
q'=0.

According to a further embodiment, the at least one alkoxysilane comprising at least one solubilizing functional group used according to the present disclosure may also have at least one of the following characteristics:
R21, R22, R'21, and R'22, which may be identical or different, are chosen from C1-C4 alkyl groups;
p=p'=1;
A and A', which may be identical or different, are chosen from linear C1-C4 alkylene groups; and/or
R23 is hydrogen.

According to this embodiment, the at least one alkoxysilane comprising at least one solubilizing functional group may be chosen from compounds of formula (V):

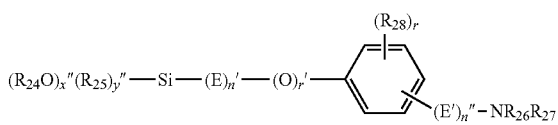
(V)

wherein:
R24 and R25, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups, x"=2 or 3,
y"=3−x",
n"=0 or 1,
n"=0 or 1,
E and E', which may be identical or different, are chosen from linear and branched C1-C20 alkylene divalent radicals,
R26 and R27, which may be identical or different, are chosen from hydrogen and linear and branched, saturated and unsaturated hydrocarbon chains, optionally comprising at least one heteroatom, optionally interrupted by or substituted with at least one entity chosen from: ether, C1-C20 alcohol ester, amine, carboxyl, alkoxysilane, C6-C30 aryl, hydroxyl, and carbonyl groups, and aromatic, heterocyclic, and non-heterocyclic rings, optionally substituted with at least one group chosen from: C1-C20 alcohol ester, amine, amide, carboxyl, alkoxysilane, hydroxyl, carbonyl, and acyl groups,
r is an integer ranging from 0 to 4,
r'=0 or 1, and
R28, which may be identical or different, is chosen from hydrogen and linear and branched, saturated and unsaturated hydrocarbon chains, comprising, for example, from 1 to 10 carbon atoms and optionally at least one heteroatom, optionally interrupted by or substituted with at least one entity chosen from: ether, C1-C20 alcohol ester, amine, carboxyl, alkoxysilane, C6-C30 aryl, hydroxyl, and carbonyl groups, and aromatic, heterocyclic, and non-heterocyclic rings, optionally substituted with at least one group chosen from: C1-C20 alcohol ester, amine, amide, carboxyl, alkoxysilane, hydroxyl, carbonyl, and acyl groups.

As defined above, R24 and R25, which may be identical or different, may be chosen from hydrocarbon chains. As used herein, the term "hydrocarbon chain" is intended to mean a chain comprising, for example, from 1 to 10 carbon atoms.

Likewise, R26 and R27 may be chosen from hydrocarbon chains. In this embodiment, the hydrocarbon chains may comprise from 1 to 10 carbon atoms.

According to another embodiment, the aromatic ring comprises from 6 to 30 carbon atoms. In a further embodiment, the aromatic ring is an optionally substituted phenyl radical.

According to at least one embodiment, the at least one alkoxysilane comprising at least one solubilizing functional group used in accordance with the present disclosure may have at least one of the following characteristics:
R24 is a C1-C4 alkyl group;
x"=3;
n'=n"=1
r=r'=0; and/or
R26 and R27, which may be identical or different, are chosen from hydrogen and groups chosen from C1-C4 alkyl groups, C1-C4 hydroxyalkyl groups, and C1-C4 aminoalkyl groups.

According to this embodiment, the at least one alkoxysilane comprising at least one solubilizing functional group may be chosen from:
3-(m-aminophenoxy)propyl trimethoxysilane, of formula:

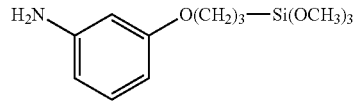

p-aminophenyl trimethoxysilane, of formula:

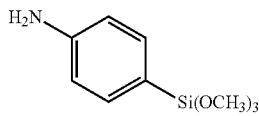

and
N-(2-aminoethylaminomethyl)phenethyl trimethoxysilane, of formula:

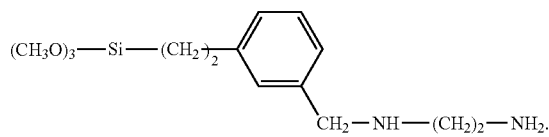

According to a further embodiment of the present disclosure, the at least one alkoxysilane comprising at least one solubilizing functional group present in the composition is chosen from compounds of formula (VI):

$$(R29O)x1(R30)y1\text{-Si-}(A1)s\text{-CH}=O \qquad (VI)$$

wherein:
R29 and R30, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups,
x1=2 or 3,
y1=3−x1,
A1 is chosen from linear and branched C1-C20 alkylene divalent radicals, optionally interrupted by or substituted with at least one group chosen from C1-C30 alcohol ester, amine, carboxyl, alkoxysilane, C6-C30 aryl, hydroxyl, and carbonyl groups, and
s=0 or 1.

As defined above, R29 and R30, which may be identical or different can be chosen from hydrocarbon chains. As used herein, the term "hydrocarbon chain" means a chain comprising, for example, from 1 to 10 carbon atoms.

In another embodiment, the at least one alkoxysilane comprising at least one solubilizing functional group may have at least one of the following characteristics:
R29 and R30, which may be identical or different, are chosen from C1-C4, alkyl groups;
s=1; and
A1 is a linear C1-C4 alkylene group According to this embodiment, the at least one alkoxysilane comprising at least one solubilizing functional group may be chosen from:
triethoxysilyl butyraldehyde, of formula:

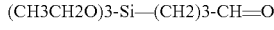

triethoxysilyl undecanal, of formula:

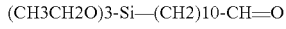

and
triethoxysilyl undecanal, ethylene glycol acetal, of formula:

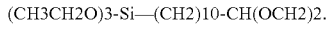

In a further embodiment, the at least one alkoxysilane comprising at least one solubilizing functional group is chosen from compounds of formula (VII):

wherein the R radicals, which may be identical or different, are chosen from C1-C6 alkyl radicals and n is an integer ranging from 1 to 6, for example, from 2 to 4.

In at least one embodiment, the at least one alkoxysilane comprising at least one solubilizing functional group present in the composition of the present disclosure is a γ-aminopropyltriethoxysilane, also known as 3-aminopropyltriethoxysilane.

Particularly preferred alkoxysilanes having at least one solubilizing functional group include alkoxysilanes comprising a silicone atom. Suitable examples include those of formula R(4-n)SiXn, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Possible examples of useful alkoxysilanes include 3-mercaptopropyltriethoxysilane and aminoalkyltrialkoxysilanes such as 3-aminopropyltriethoxysilane, as described in French Patent Application No. FR 2 789 896.

Other useful alkoxysilanes are cited, for example, in Patent Application EP 1 216 022, which describes alkoxysilanes comprising at least one hydrocarbon chain containing a non-basic solubilizing chemical function. In this respect, non-limiting mention may be made of the HCl-neutralized sodium N-[(3-trimethoxysilyl)propyl]ethylenediaminetriacetate supplied by GELEST.

According to at least one embodiment, the alkoxysilanes may comprise at least one hydrocarbon chain containing fluorine atoms. Possible examples include but are not limited to the 3,3,3-trifluoropropyltriethoxysilane or tridecafluorooctyltriethoxysilane compounds described in Patent Application EP 1 510 197.

In another embodiment, the useful alkoxysilanes may be alkoxysilanes which carry a group having a cosmetic functional group, such as aromatic nitro dyes or anthraquinone, napthoquinone, benzoquinone, azo, xanthene, triarylmethane, azine, indoaniline, indophenolic or indoamine dyes; groups having a reductive effect, such as thiol groups, sulphinic acid or sulphinic salt, it being possible for these alkoxysilanes to carry a solubilizing non-hydrolysable group such as amino groups, carboxylic acids, sulphonic acids, sulphates, quaternary ammoniums, polyalcohols, polyether and phosphates. One possible example includes aminopropyl-N-(4,2-dinitrophenyl)aminopropyldiethoxysilane. Compounds of this kind are described, for example, in Patent Application EP 1 216 023.

The alkoxysilanes of the present disclosure may be amino aryl alkoxysilanes. Possible examples include but are not limited to the following compounds:
3-(m-aminophenoxy)propyltrimethoxysilane, of the formula:

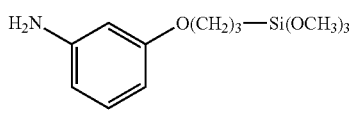

provided by GELEST,
p-aminophenyltrimethoxysilane, of formula:

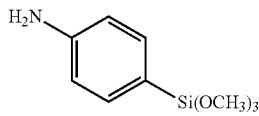

provided by GELEST, and
N-(2-aminoethylaminomethyl)phenethyltrimethoxysilane, of the formula:

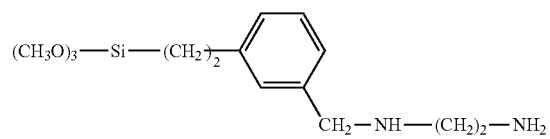

provided by GELEST.

According to at least one embodiment, the at least one organic silicon compound is N-(2-aminoethylaminomethyl) phenethyltrimethoxysilane.

The alkoxysilanes of the present disclosure may also be silanes having an aldehyde or acetal functional group, such as the triethoxysilylbutyraldehyde of formula (CH3CH2O)2Si(CH2)5CHO or the triethoxysilylunedecanol ethylene glycol acetal (CH3CH2O)3Si(CH2)10CH(OCH2)2, which are provided by GELEST.

The alkoxysilanes may also be silanes containing non-primary amines, such as the bis[3-(triethoxysilyl)propyl]amine of the formula (CH3CH2O)3-Si(CH2)3NH(CH2)3Si(OCH2CH3)3 provided by Fluorochem, the bis[trimethoxysilylpropyl]amine of the formula (CH3O)3-Si(CH2)3NH(CH2)3Si(OCH3)3 provided by Gelest, the bis[methyldiethoxysilylpropyl]amine of the formula (CH3CH2O)2CH3Si(CH2) 3NH(CH2)3SiCH3(OCH2CH3)2 provided by Gelest and the bis[3-trimethoxysilylpropyl]ethylenediamine of formula (CH3O)3Si(CH2)3NH(CH)2NH(CH2)3Si(OCH3)3 provided by Gelest.

In another embodiment the at least one alkoxysilane is a trialkoxysilane comprising an amino substituent.

In at least one embodiment, the at least one alkoxysilane comprising at least one solubilizing functional group present in the composition of the present disclosure is a γ-aminopropyltriethoxysilane, also known as 3-aminopropyltriethoxysilane.

The at least one reactive agent is employed in the composition of the invention in an amount ranging from about 0.01 to about 5% by weight, such as from about 0.05 to about 3% by weight, and from about 0.1 to about 2% by weight, based on the total weight of the nail polish composition.

Solvent

The nail polish composition of the present invention also includes at least one solvent chosen from at least one volatile solvent and water. Any solvent typically found in nail polish compositions can be used. Suitable solvents include, but are not limited to, organic solvents which are liquid at ambient temperature. Examples of suitable volatile solvents include, but are not limited to, ketones such as methyl ethyl ketone, methyl isobutyl ketone, diisobutyl ketone, isophorone, cyclohexanone or acetone; alcohols, such as ethanol, iso-propanol, diacetone alcohol, 2-butoxyethanol or cyclohexanol; glycols, such as ethylene glycol, propylene glycol, pentylene glycol or glycerol; propylene glycol ethers, such as propylene glycol monomethyl ether, propylene glycol monomethyl ether acetate or dipropylene glycol mono(n-butyl)ether; short-chain esters (having a total of 2 to 7 carbon atoms), such as ethyl acetate, methyl acetate, propyl acetate, n-butyl acetate or isopentyl acetate; alkanes, such as decane, heptane, dodecane or cyclohexane; aldehydes, such as benzaldehyde or acetaldehyde; and their mixtures. Most preferred are short-chain esters (having a total of from 2 to 8 carbon atoms).

In the event that water is also employed as one of the solvents, the compositions of the present invention qualify as emulsions and, as such, the compositions of the present invention thereby lend themselves to the addition of water-soluble materials.

In accordance with preferred embodiments, the at least one solvent, is preferably present in the composition in an amount of from about 1% to about 90% by weight, preferably from about 10% to about 80% by weight, preferably from about 30 to about 75% by weight, including all ranges and subranges therebetween, all weights based on the total weight of the composition.

Plasticizer

According to particularly preferred embodiments of the present invention, compositions further comprising at least one plasticizer are provided. Any plasticizing agent typically found in nail polish compositions can be used. Examples of suitable plasticizers include, but are not limited to, glycols and their ether or ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, and mixtures thereof.

In accordance with preferred embodiments, the plasticizer, is preferably present in the composition in an amount of from about 0.01% to about 25% by weight, preferably from about 0.1% to about 22% by weight, preferably from about 1 to about 20% by weight, including all ranges and subranges therebetween, all weights based on the total weight of the nail polish composition.

Colorant

According to particularly preferred embodiments of the present application, compositions further comprising at least one colorant are provided. Any colorant typically found in nail polish compositions can be used. Suitable colorants include, but are not limited to, lipophilic dyes, pigments and pearlescent agents, and their mixtures.

Suitable examples of fat-soluble dyes are, for example, Sudan red, DC Red 17, DC Green 6, β-carotene, soybean oil, Sudan brown, DC Yellow 11, DC Violet 2, DC Orange 5 and quinoline yellow.

Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescent pigments can be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

In accordance with preferred embodiments, the colorant, if present, is preferably present in the composition in an amount of from about 0.01% to about 20% by weight, preferably from about 0.1% to about 15% by weight, preferably from about 0.5 to about 10% by weight, including all ranges and subranges therebetween, all weights based on the total weight of the composition.

Auxiliaries/Additives

The nail polish composition of the present invention may additionally comprise an additive or auxiliary commonly used in cosmetic compositions and known to a person skilled in the art as being capable of being incorporated into a nail polish composition. Such additives or auxiliaries may be chosen from thickeners, coalescents, preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, proteins, ceramides, plant extracts, fibers, and the like, and their mixtures.

A person skilled in the art will take care to select the optional additional additives and/or the amounts thereof such that the advantageous properties of the composition according to the invention are not, or are not substantially, adversely affected by the envisaged addition.

These substances may be selected variously by the person skilled in the art in order to prepare a composition which has the desired properties, for example, good adhesion or long wear.

Needless to say, the composition of the invention should be cosmetically or dermatologically acceptable, i.e., it should contain non-toxic physiologically acceptable components. The composition may be in any galenic form normally employed in the cosmetic and dermatological fields which is suitable for topical administration onto nails.

One particularly preferred embodiment of the present invention is a composition for application to nails which is substantially free of nitrocellulose (that is, less than 5% of nitrocellulose), essentially free of nitrocellulose (that is, less than 2% nitrocellulose), or free of nitrocellulose (that is, less than 0.25% nitrocellulose).

The inventors have found that when the styrene maleic anhydride copolymer reacts with the at least one reactive agent, a resultant composition having surprising and unexpected long-wear properties is formed. Moreover, it has also been surprisingly found that the resultant compositions provide a degree of gloss that is at least comparable, and oftentimes higher, than that of conventional nitrocellulose-containing compositions.

According to other preferred embodiments of the present invention, methods of making up or protecting nails comprising applying a composition of the present invention to nails in an amount sufficient to makeup or protect the nails are provided. "Making up" as used herein means to provide decoration (for example, color) to the nail. "Protecting" as used herein means to inhibit damage to the nail (for example, chipping) by providing a protective layer on the nail. The application process involves one or more applications or coatings of the nail polish compositions of the present invention to the desired area as needed.

The compositions according to the invention can be manufactured by known processes used generally in the cosmetics or dermatological field.

The following examples are intended to illustrate the invention without limiting the scope as a result. The percentages are given on a weight basis.

EXAMPLES

Example 1

| Phase | RM Name | Concentration (%) |
|---|---|---|
| A | Styrene Maleic Copolymer (SMA 2021 prep) | 19.75 |
| A | Ethyl Acetate | 9.875 |
| A | Propyl Acetate | 19.975 |
| A | Butyl Acetate | 14.225 |
| A | Tosylamide Epoxy Resin | 12.375 |
| A | Toyo Ink Red 7 | 3.0 |
| B | POLYETHYLENE IMINE (PEI; PM: 1700) | 0.20 |
| B | DI Water | 20.2 |
| C | Polyurethane (Baycusan C1004: PU-35) | 0.4 |
| | Total | 100 |

1. The ingredients of phase A were combined and mixed.
2. Polyethyleneimine in water was added to Phase A while mixing.
3. The polyurethane was added to the combined phases while mixing.

Example 2

| Phase | RM Name | Concentration (%) |
|---|---|---|
| A | Styrene Maleic Copolymer (SMA 2000 Prep) | 17.78 |
| A | Ethyl Acetate | 10.86 |
| A | Propyl Acetate | 21.21 |
| A | Butyl Acetate | 14.42 |
| A | Tosylamide Epoxy Resin | 12.23 |
| B | POLYETHYLENE IMINE (PEI; PM: 1700) | 0.25 |
| B | Toyo Ink Red 7 | 3.0 |
| B | DI Water | 20.25 |
| | Total | 100 |

1. The ingredients of phase A were combined and mixed.
2. Polyethyleneimine in water was added to Phase A while mixing.

Example 3

| Phase | RM Name | Example 3-1 Concentration (%) | Example 3-2 Concentration (%) | Example 3-3 Concentration (%) |
|---|---|---|---|---|
| A | Styrene Maleic Copolymer (SMA 1000P prep) | 17.5 | 20.0 | 15.0 |
| A | Ethyl Acetate | 14.67 | 18.42 | 15 |
| A | Propyl Acetate | 14.67 | 18.42 | 15 |
| A | Butyl Acetate | 9.83 | 7.33 | 7 |
| A | IPA solvent | 0 | 0 | 7.0 |
| A | Tosylamide Epoxy Resin | 17.5 | 10.0 | 15.0 |
| A | Toyo Ink Red 7 | 0 | 0 | 3.0 |
| B | Aminopropyltriethoxysilane (APTES) | 0.25 | 0.25 | 1.0 |
| B | DI Water | 25.58 | 25.58 | 22 |
|   | Total | 100 | 100 | 100 |

1. The ingredients of phase A were combined and mixed.
2. The aminopropyltriethoxysilane in water was added to Phase A while mixing.

Example 4

Comparative Example

| | A1 Concentration (%) | A2 Concentration (%) | B1 Concentration (%) | B2 Concentration (%) | C1 Concentration (%) | C2 Concentration (%) | C3 Concentration (%) | C4 Concentration (%) |
|---|---|---|---|---|---|---|---|---|
| RM Name | | | | | | | | |
| SMA 2000 (Styrene Maleic Anhydride Copolymer) PREP | 30 | 30 | 0 | 0 | 15 | 15 | 15 | 15 |
| ETHYL ACETATE | 30 | 30 | 25 | 25 | 27.5 | 27.5 | 27.5 | 27.5 |
| PROPYL ACETATE | 30 | 30 | 25 | 25 | 27.5 | 27.5 | 27.5 | 27.5 |
| BUTYL ACETATE | 9.8 | 9.5 | 19.8 | 19.5 | 14.8 | 14.5 | 15 | 14 |
| APTES (AMINOPROPYL TRIETHOXYSILANE) | 0.2 | 0.5 | 0.2 | 0.5 | 0.2 | 0.5 | 0 | 1 |
| TOSYLAMIDE/ EPOXY RESIN (75% resin in 25% Butyl acetate) | 0 | 0 | 30 | 30 | 15 | 15 | 15 | 15 |
| Total | 100 | 100 | 100 | 100 | 100 | 100 | 100 | 100 |
| Hardness | | | | | | | | |
| T1 | Not measurable | Not measurable | Not measurable | Not measurable | 208 | 208 | 234 | 219 |
| T2 | Not measurable | Not measurable | Not measurable | Not measurable | 194 | 197 | 242 | 206 |
| T3 | Not measurable | Not measurable | Not measurable | Not measurable | 195 | 189 | 225 | 229 |
| Average | | | | | 199 | 198 | 233.67 | 218 |
| Visual Check | Clear | Clear | Clear | Clear | Clear | Clear | Clear | Clear |

What is claimed is:

1. A nail polish composition, comprising:
   a. at least one high gloss film forming agent which is a styrene maleic anhydride copolymer in an amount of from about 1 to about 40% by weight, based on the total weight of the composition;
   b. at least one co-film forming agent which is an epoxy resin;
   c. at least one reactive agent which is a polyalkyleneamine in an amount of from about 0.01 to about 5% by weight, based on the total weight of the composition; and
   d. at least one solvent selected from the group consisting of a volatile solvent, water, and mixtures thereof,
   wherein the composition is cosmetically acceptable and wherein the composition does not require use of nitrocellulose.

2. The composition of claim 1, wherein (a) has a Tg ranging from about 100° C. to about 175° C.

3. The composition of claim 1, wherein (a) has a molecular weight ranging from about 1,000 to about 200,000.

4. The composition of claim 1, wherein (b) has a Tg of less than about 100° C.

5. The composition of claim 1, wherein (b) is present in an amount of from about 0.1 to about 50% by weight, based on the total weight of the composition.

6. The composition of claim 1, wherein the weight ratio of (a) to (b) is about 1 to 1.

7. The composition of claim 1, wherein (c) is present in an amount of from about 0.05 to about 3% by weight, based on the total weight of the composition.

8. The composition of claim 1, wherein the at least one volatile solvent is chosen from ethyl acetate, propyl acetate, butyl acetate, and mixtures thereof.

9. The composition of claim 1, wherein (d) is present in an amount of from about 1 to about 90% by weight, based on the total weight of the composition.

10. The composition of claim 1, further comprising at least one plasticizer in an amount of from about 0.01 to about 25% by weight, based on the total weight of the composition.

11. The composition of claim 1, wherein the styrene maleic anhydride copolymer is present in an amount ranging from 1 to about 20% by weight, based on the total weight of the composition.

12. The composition of claim 1, wherein the polyalkyleneamine is a polyalkyleneimine and is present in an amount ranging from about 0.1 to about 2% by weight, based on the total weight of the composition.

13. The composition of claim 1, wherein the composition is anhydrous.

14. A method of making up finger nails comprising applying onto the nails a nail polish composition, comprising:
   a. at least one high gloss film forming agent which is a styrene maleic anhydride copolymer in an amount of from about 1 to about 40% by weight, based on the total weight of the composition;
   b. at least one co-film forming agent which is an epoxy resin;
   c. at least one reactive agent which is a polyalkyleneamine in an amount of from about 0.01 to about 5% by weight based on the total weight of the composition; and
   d. at least one solvent selected from the group consisting of a volatile solvent, water, and mixtures thereof, wherein the composition is cosmetically acceptable and wherein the composition does not require use of nitrocellulose.

15. The method of claim 14, wherein the styrene maleic anhydride copolymer has a Tg ranging from about 100° C. to about 175° C.

16. The method of claim 14, wherein the styrene maleic anhydride copolymer has a molecular weight ranging from about 1,000 to about 200,000.

17. The method of claim 14, wherein the epoxy resin has a Tg of less than about 100° C.

18. The method of claim 14, wherein the epoxy resin is present in an amount of from about 0.1 to about 50% by weight, based on the total weight of the composition.

19. The method of claim 14, wherein the weight ratio of the styrene maleic anhydride copolymer to the epoxy resin is about 1 to 1.

20. The method of claim 14, wherein the at least one reactive agent polyalkyleneamine is present in an amount of from about 0.05 to about 3% by weight, based on the total weight of the composition.

21. The method of claim 14, wherein the at least one volatile solvent is chosen from ethyl acetate, propyl acetate, butyl acetate, and mixtures thereof.

22. The method of claim 14, wherein the at least one volatile solvent is present in an amount of from about 1 to about 90% by weight, based on the total weight of the composition.

23. The method of claim 14, wherein the nail polish composition further comprises at least one plasticizer in an amount of from about 0.01 to about 25% by weight, based on the total weight of the composition.

24. The composition of claim 11, wherein the polyalkyleneamine is a polyalkyleneimine and is present in an amount ranging from about 0.1 to about 2% by weight, based on the total weight of the composition.

* * * * *